US005721320A

United States Patent [19]
Priddy et al.

[11] Patent Number: 5,721,320
[45] Date of Patent: Feb. 24, 1998

[54] IN SITU BLOCK COPOLYMER FORMATION DURING POLYMERIZATION OF A VINYL AROMATIC MONOMER

[75] Inventors: Duane B. Priddy; Irene Q. Li, both of Midland, Mich.

[73] Assignee: The Dow Chemical Company, Midland, Mich.

[21] Appl. No.: 810,878

[22] Filed: Mar. 5, 1997

[51] Int. Cl.$^6$ .................... C08F 255/10; C08F 2/38
[52] U.S. Cl. .................... 525/316; 525/314; 525/259; 526/204
[58] Field of Search .................... 525/316, 314, 525/259; 526/204

[56] References Cited

U.S. PATENT DOCUMENTS

| 5,322,912 | 6/1994 | Georges et al. | 526/204 |
| 5,401,804 | 3/1995 | Georges et al. | 525/267 |
| 5,549,998 | 8/1996 | Georges et al. | 430/109 |

OTHER PUBLICATIONS

Polymer Preprints, "Synthesis, Characterization, and Evaluation of Initiators for Living Free Radical Polymerization: Synthesis of Polystyrene with Controlled Structure", Irene Li et al., vol. 36, No. 1 pp. 469–470 (1995).

Macromolecules, "Narrow Molecular Weight Resins by a Free-Radical Polymerization Process", M.K. Georges et al., 26, 2987–2988, (1993).

J. Am. Chem. Soc., "Molecular Weight Control by a Living Free-Radical Polymerization Process", C.J. Hawker, 116, 11185–11186, (1994).

Chemistry in Australia, "Living"Free Radical Polymerization, E. Rizzardo, p. 32 (1987).

J. Org. Chem., "Reaction of n-Butyllithium and 2,2,6,6-Tetramethylpiperidine Nitroxyl". G.M. Whitesides et al., vol. 40, No. 23, pp. 3448–3450, (1975).

Makromol. Chem., Rapid Commun., "Reactions of Benzoyloxyl Radicals with Some Common Vinyl Monomers", Graeme Moad et al., pp.533–536(1992).

*Primary Examiner*—Irina S. Zemel

[57] ABSTRACT

The present invention is a free radical bulk polymerization process for producing a rubber modified polymer from a vinyl aromatic monomer comprising:

polymerizing the vinyl aromatic monomer in the presence of a diene rubber having at least one stable free radical group, under polymerization conditions such that a vinyl aromatic-diene block and/or graft copolymer rubber is formed.

10 Claims, No Drawings

IN SITU BLOCK COPOLYMER FORMATION DURING POLYMERIZATION OF A VINYL AROMATIC MONOMER

This application claims the benefit of U.S. Provisional Application No. 60/014,616, filed Mar. 29, 1996.

BACKGROUND OF THE INVENTION

The present invention relates to rubber modified polymers obtained from vinyl aromatic monomers.

Rubber modified polymers have been produced from vinyl aromatic monomers by a number of processes for the purpose of improving impact resistance. Typically, a rubber is blended with a polymerized vinyl aromatic monomer, or alternatively, the vinyl aromatic monomer is polymerized in the presence of a rubber. In the latter method, the vinyl aromatic monomer is partially graft polymerized onto the rubber. However, the amount of grafting and molecular weight of the grafting chain is difficult to control, which can negatively influence the gloss and impact properties.

Rubber modified copolymers of vinyl aromatic monomers have also been produced, such as acrylonitrile-butadiene-styrene (ABS). ABS copolymers have been produced using polymerization processes such as bulk-suspension, continuous bulk, and emulsion. Emulsion polymerization processes typically produce products having the best balance of gloss and impact strength, however bulk processes are favored due to lower cost.

Other rubbers are also used in bulk polymerization processes to improve the gloss and/or impact properties, including styrene-butadiene block copolymer rubbers. However, these rubbers are typically more expensive and are needed in higher amounts than conventional polybutadiene rubbers.

Therefore, there remains a need for a more efficient and cost effective process for producing a rubber modified polymer from a vinyl aromatic monomer, having excellent balance of gloss and impact properties.

SUMMARY OF THE INVENTION

The present invention is a free radical bulk polymerization process for producing a rubber modified polymer from a vinyl aromatic monomer comprising:

polymerizing the vinyl aromatic monomer in the presence of a diene rubber having at least one stable free radical group, under polymerization conditions such that a vinyl aromatic-diene block and/or graft copolymer rubber is formed.

This process produces block and/or graft copolymers in situ during the polymerization of the vinyl aromatic monomer and allows for the production of rubber reinforced polymers without the high cost of block or pregrafted diene rubbers.

DESCRIPTION OF THE PREFERRED EMBODIMENTS

One embodiment of the present invention is a process for producing rubber modified polymers from vinyl aromatic monomers. Vinyl aromatic monomers suitable for use according to the present invention include vinyl aromatic monomers previously known for use in polymerization processes, such as those described in U.S. Pat. Nos. 4,666,987, 4,572,819 and 4,585,825, which are incorporated herein by reference. Preferably, the monomer is of the formula:

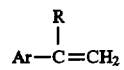

wherein R is hydrogen or methyl, Ar is an aromatic ring structure having from 1 to 3 aromatic rings with or without alkyl, halo, or haloalkyl substitution, wherein any alkyl group contains 1 to 6 carbon atoms and haloalkyl refers to a halo substituted alkyl group. Preferably, Ar is phenyl or alkylphenyl with phenyl being most preferred. Typical vinyl aromatic monomers which can be used include: styrene, alpha-methylstyrene, all isomers of vinyl toluene, especially paravinyltoluene, all isomers of ethyl styrene, propyl styrene, vinyl biphenyl, vinyl naphthalene, vinyl anthracene and the like, and mixtures thereof. The vinyl aromatic monomers may also be combined with other copolymerizable monomers. Examples of such monomers include, but are not limited to acrylic monomers such as acrylonitrile, methacrylonitrile, methacrylic acid, methyl methacrylate, acrylic acid, and methyl acrylate; maleimide, phenylmaleimide, and maleic anhydride.

The rubber used in the process of the present invention is a diene rubber having at least one stable free radical group. The rubber can be prepared from a diene monomer component and a stable free radical component. Typically, the diene monomer is polymerized under anionic or free radical polymerization conditions in the presence of the stable free radical component. Preferably, the diene monomer component is a 1,3-conjugated diene such as butadiene, isoprene, piperylene, chloroprene and the like. Most preferably, the diene monomer component is 1,3-butadiene. The stable free radical component is a stable free radical containing compound which will react with a diene monomer or a diene rubber. The stable free radical containing compound can be a stable free radical which is storage stable in pure form, i.e. nonreactive with itself at temperatures of up to 120° C., a compound derived therefrom, or any compound which will react with the diene monomer or rubber and contains a stable free radical group. Typically, the stable free radical component is a chain transfer agent, an initiator, a terminating agent or a comonomer which contains a stable free radical group.

The stable free radical group is defined as a substituent which is capable of forming a stable free radical upon activation. For activation of the stable free radical group to occur, the radical forming atom of the stable free radical group is typically bonded to the diene rubber through an activated carbon. The stable free radical group-activated carbon bond is typically stable at temperatures up to 50° C. An activated carbon atom is defined as a carbon atom which is bonded to at least one unsaturated or aromatic carbon such as those found in alkenyl, cyano, carboxyl, aryl, carboalkoxy (—C(=O)—OR), or carboamine (—C(=O)—NR$_2$) groups. At temperatures above about 60° C., the stable free radical group activates to form a stable free radical. For example, a compound containing —C*—O—N< as the stable free radical group, wherein the C* atom is activated or bonded to a unsaturated carbon atom, will activate at temperatures above about 60° C. to form a O—N< and carbon radical pair. If activation of the stable free radical group occurs during the polymerization of a vinyl aromatic monomer, the vinyl aromatic monomer will react with the carbon radical and become inserted between the O of the stable free radical and the activated carbon, resulting in the formation of a vinyl aromatic polymer segment, e.g. —C*-(poly(vinyl aromatic monomer))-O—N<.

Typically, the diene rubber containing the stable free radical group is a polybutadiene rubber containing a nitroxy substituent bonded to the polybutadiene rubber through an activated carbon (polybutadiene—R—C*—O—N<). Examples of nitroxy containing stable free radicals which form upon activation of the stable free radical group include:
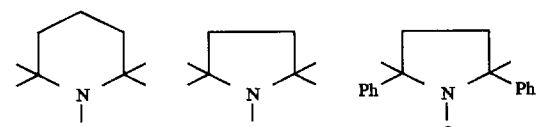
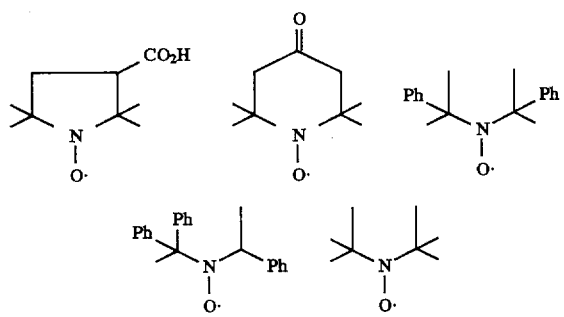
Examples of compounds which contain nitroxy stable free radical groups include:
Chain Transfer Agents:
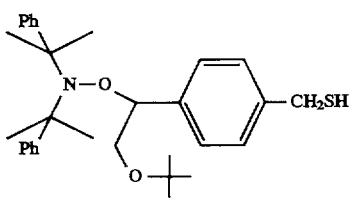
-continued
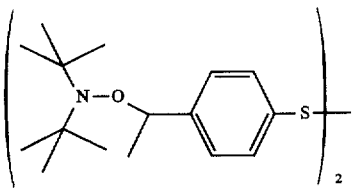
Terminating Agents:
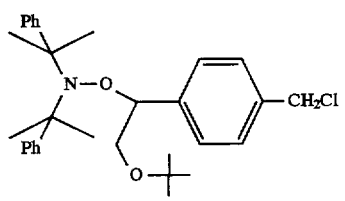
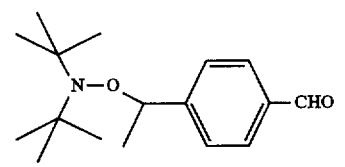
Initiators:
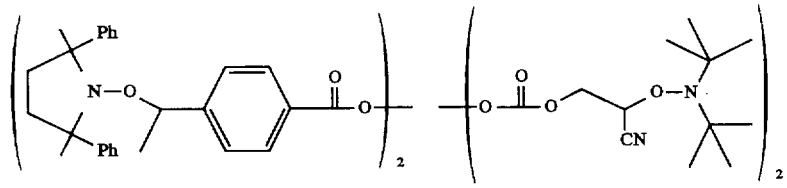
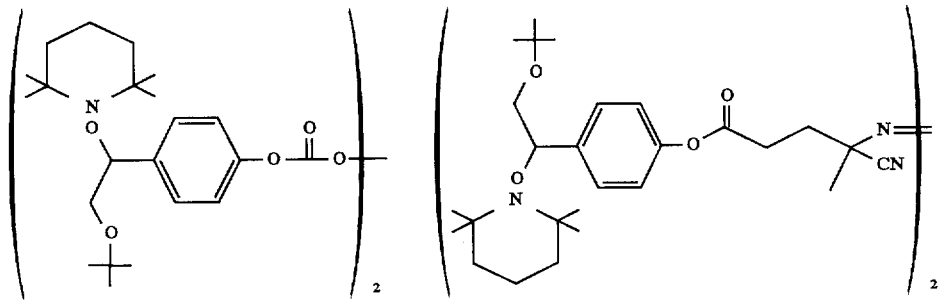

-continued

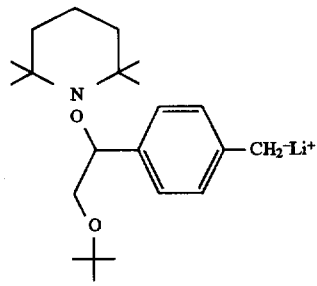

Comonomers:

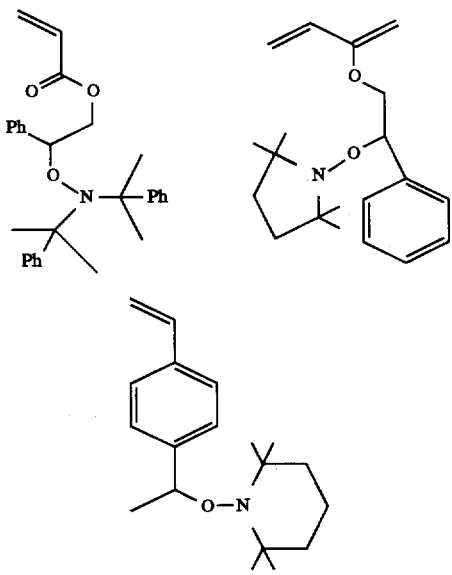

Other nitroxy containing compounds can be found in U.S. Pat. No. 4,521,429 by Solomon et al. which is incorporated herein by reference.

Nitroxy containing compounds can be prepared from the desired precursors, by forming carbon centered radicals in the presence of a nitroxy containing compound which traps the carbon centered radical intermediates as they form. Methods of making carbon centered radicals are well known in the art and include techniques such as 1) H-abstraction from activated hydrogen compounds as discussed in ACS Polym. Prepr. 1995, 36, 469 by L Li, B. A. Howell; A. Ellaboudy; P. Kastl; and D. B. Priddy; 2) radical addition to activated double bonds as discussed in Macromolecules 1993, 26, 2987 by M. K. Georges, R. P. N. Veregin, P. M. Kazmaier, and G. K. Hamer; 3) electron transfer as disclosed in J. Organic Chemistry 1975, 40, 3448 by G. M. Whitesides and T. L. Newirth; and 4) thermolysis of an activated azo compound as discussed in U.S. Pat. No. 4,581,429 by Solomon et al., EP-304756 by Solomon et al., and Chemistry in Australia, Jan–Feb. 1987, 32, by E. Rizzardo.

Methods of polymerizing dienes in the presence of chain transfer agents, initiators, terminating agents or comonomers are well known in the art and any method may be utilized in preparing the diene rubbers used in the process of the present invention.

In one embodiment of the present invention, styrene-butadiene-styrene copolymer rubber is produced in situ by polymerizing styrene monomer in the presence of a polybutadiene containing a nitroxyl stable free radical group, to produce a rubber modified polystyrene. The polybutadiene containing a nitroxyl stable free radical group can be prepared by anionically polymerizing butadiene in the presence of an initiator such as butyl lithium. A group containing an activated carbon is added by reacting the lithium terminated polybutadiene with a small amount of styrene monomer, such that an oligomer having an end group containing an activated carbon atom, e.g. a secondary benzylic carbon, is attached to the polybutadiene chain. The polybutadiene-styrene oligomer is then reacted with a nitroxy stable free radical such as 2,2,6,6-tetramethylpiperidinyl-1-oxy (TEMPO) to produce a polybutadiene containing a nitroxy stable free radical group bonded to the polybutadiene through an activated carbon atom.

An alcohol containing a nitroxy group can be converted to a nitroxy containing terminating agent by reacting the alcohol with a sulfonic acid halide, e.g. tosyl chloride, and polybutadienyllithium to produce a polybutadiene having nitroxy functional groups. Alcohols containing nitroxy groups are known in the art and can be prepared as disclosed in "Architectural control in "living" free radical polymerizations: preparation of star and graft polymers", Angew. Chem. Int. Ed. Engl. (1995), 34 (13/14), 1456-9 by Hawker.

A nitroxy functional alcohol can also be reacted with a haloalkylstyrene, e.g. p-chloromethylstyrene, to produce a nitroxy containing monomer. The monomer is then heated with a diene, e.g. butadiene, in the presence of an initiator, e.g. butyllithium, to produce a polybutadiene containing pendant nitroxy groups.

The weight average molecular weight (Mw) of the diene polymer chain is typically from about 20,000 to about 300,000, preferably from about 50,000 to about 250,000, more preferably from about 75,000 to about 200,000 and most preferably from about 100,000 to about 150,000.

The resultant diene polymer can contain stable free radical groups which are pendant from the polymer chain and/or on one or both chain ends. Typically, the functionalized diene rubber contains at least 1 stable free radical group for every 2,000, preferably for every 1,000, more preferably for every 500, and most preferably for every 200 diene monomer units.

The rubber reinforced polymer can be prepared by dissolving the diene rubber containing a stable free radical group in a vinyl aromatic monomer and polymerizing the rubber/monomer mixture. This process can be conducted using conventional techniques known in the art for preparing rubber reinforced polymers such as high impact polystyrene (HIPS) and ABS, which are described in U.S. Pat. Nos. 2,646,418, 4,311,819 and 4,409,369 and are incorporated herein by reference.

The amount of rubber added to the vinyl aromatic monomer is typically from about 3 to about 20 percent, preferably from about 5 to about 15 percent and more preferably from about 7 to about 12 percent based on the total weight of the vinyl aromatic monomer and the rubber.

Initiators may also be used in the process of the present invention. Useful initiators include free radical initiators such as peroxide and azo compounds which will accelerate the polymerization of the vinyl aromatic monomer. Suitable initiators include but are not limited to tertiary butyl peroxyacetate, dibenzoyl peroxide, dilauroyl peroxide, t-butylhydroperoxide, ditertiary-butylperoxide, cumene hydroperoxide, dicumylperoxide, 1,1-bis(tertiary-butylperoxy)-3,3,5-trimethyl-cyclohexane, t-butylperoxybenzoate, 1,1-bis(t-butylperoxy)-cyclohexane, benzoylperoxide, succinoylperoxide and t-butylperoxypivilate, and azo compounds such as azobisisobutyro-nitrile, azobis-2,4-dimethylvaleronitrile, azobiscyclohexanecarbo-nitrile, azobismethyl isolactate and azobiscyanovalerate. Typical amounts are well known in the art and may be used in the process of the present invention.

Initiators may be employed in a range of concentrations dependent on a variety of factors including the specific initiators employed, the desired levels of polymer grafting and the conditions at which the mass polymerization is conducted. Typically from 50 to 2000, preferably from 100 to 1500, parts by weight of the initiator are employed per million parts by weight of monomer.

Additionally, a solvent may be used in the process of the present invention. Acceptable solvents include normally liquid organic materials which form a solution with the rubber, vinyl aromatic monomer and the polymer prepared therefrom. Representative solvents include aromatic and substituted aromatic hydrocarbons such as benzene, ethylbenzene, toluene, xylene or the like; substituted or unsubstituted, straight or branched chain saturated aliphatics of 5 or more carbon atoms, such as heptane, hexane, octane or the like; alicyclic or substituted alicyclic hydrocarbons having 5 or 6 carbon atoms, such as cyclohexane; and the like. Preferred solvents include substituted aromatics, with ethylbenzene and xylene being most preferred. In general, the solvent is employed in amounts sufficient to improve the processability and heat transfer during polymerization. Such amounts will vary depending on the rubber, monomer and solvent employed, the process equipment and the desired degree of polymerization. If employed, the solvent is generally employed in an amount of up to about 35 weight percent, preferably from about 2 to about 25 weight percent, based on the total weight of the solution.

Other materials may also be present in the process of the present invention, including plasticizers, e.g. mineral oil; flow promoters, lubricants, antioxidants, e.g. alkylated phenols such as di-tertbutyl-p-cresol or phosphites such as trisnonyl phenyl phosphite; catalysts, e.g. acidic compounds such as camphorsulfonic acid or 2-sulfoethylmethacrylate; mold release agents, e.g. zinc stearate, or polymerization aids, e.g. chain transfer agents such as an alkyl mercaptan, e.g. n-dodecyl mercaptan. If employed, the chain transfer agent is generally employed in an amount of from about 0.001 to about 0.5 weight percent based on the total weight of the polymerization mixture to which it is added.

During the polymerization of the rubber/monomer mixture, the vinyl aromatic monomer polymerizes to form a matrix phase and grafts onto the diene rubber. The majority of the grafting will occur via any stable free radical groups which are pendant from the diene polymer chain. However, some grafting of the vinyl aromatic monomer may occur directly onto the diene polymer chain as typically occurs during these types of conventional polymerization processes.

The Mw of the grafted polymer inserted between the stable free radical groups and the activated carbon atom is typically less than half of the Mw of the matrix phase, preferably less than 25 percent, more preferably less than 20 percent, and most preferably less than 15 percent. Typically, the Mw of the grafted polymer is from about 15,000 to about 150,000, preferably from about 25,000 to about 100,000, more preferably from about 25,000 to about 75,000, and most preferably from about 30,000 to about 60,000.

The Mw of the matrix phase can vary greatly dependent upon the applications of the rubber modified polymer. Typically, the Mw can vary from 50,000 to about 300,000.

The process of the present invention is particularly useful in preparing high impact polystyrene and acrylonitrile-butadiene-styrene polymers wherein the rubber is typically dispersed throughout the polystyrene or polystyrene-acrylonitrile matrix phase. These polymers can be used in a variety of applications including injection molding and thermoforming of refrigerator liners, household appliances, toys, and furniture.

In a specific embodiment of the present invention a rubber modified polystyrene is made by polymerizing styrene in the presence of a nitroxy terminated polyisoprene, such that polyisoprene/polystyrene block copolymers are prepared in situ during the styrene polymerization. A nitroxy terminated polyisoprene, e.g. 2,2,6,6-tetramethyl-1-piperidenyl-1-oxy terminated polyisoprene, can be prepared by polymerizing a solution of 4,4'-azobis(4-cyanoisovaleryl-2-phenyl-2',2',6', 6'-tetramethyl-1-piperidinyloxyethyl) in isoprene. The 4,4'-azobis(4-cyanoisovaleryl-2-phenyl-2',2',6',6'-tetramethyl-1-piperidinyloxyethyl) can be prepared by dissolving a nitroxy containing compound, e.g. (2,2,6,6-tetramethyl-1-piperidenyl)oxybenzeneethanol (CAS registry no. 161776-41-6) in an organic solvent and reacting with 4,4'-azobis(4-cyanoisovaleryl chloride). 4,4'-Azobis(4-cyanoisovaleryl chloride) can be produced by reacting 4,4'-azobis(4-cyanoisovaleric acid) with thionyl chloride. (2,2,6,6-tetramethyl-1-piperidinyl)oxybenzeneethanol can be produced by hydrolyzing 1-benzoxyl-2-phenyl-2-(2',2',6',6'-tetramethyl-1-piperidinyloxyl)ethane in refluxing ethanolic potassium hydroxide solution. The 1-benzoxyl-2-phenyl-2-(2',2',6',6'-tetramethyl-1-piperidinyloxyl)ethane can be prepared by heating styrene, benzoyl peroxide and 2,2,6,6,-tetramethylpiperidinyl-1-oxy (TEMPO).

In another specific embodiment of the present invention, ABS is made by copolymerizing styrene and acrylonitrile in the presence of a nitroxy terminated polybutadiene, such that butadiene-SAN block copolymers are prepared in situ during the styrene and acrylonitrile copolymerization. A nitroxy terminated polybutadiene, e.g. 2,2,6,6-tetramethyl-1-piperidenyl-1-oxy terminated polybutadiene, can be prepared by terminating polybutadienyllithium using 2,2,6,6-tetramethyl-1-[2-(oxiranylmethoxy)-1-phenylethoxy]-piperidine (I). This can be prepared by coupling epichlorohydrine with (2,2,6,6-tetramethyl-1-piperidinyl) oxy-benzeneethanol.

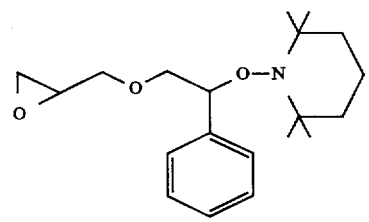

I

Additionally, the process of the present invention can be used to produce transparent rubber reinforced polymers. These polymers typically contain dense rubber particles having a volume average particle size of less than 0.1μ. Methods of particle sizing are well known by those skilled in the art.

The following examples are provided to illustrate the present invention. The examples are not intended to limit the scope of the present invention and they should not be so interpreted. Amounts are in weight parts or weight percentages unless otherwise indicated.

EXAMPLE 1

Preparation of Transparent Impact Polystyrene

Step 1: Preparation of 2,2,6,6-Tetramethyl-1-[2-(oxiranylmethoxy)-1-phenylethoxy]Piperidine (I).

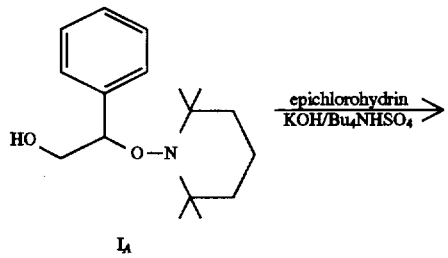

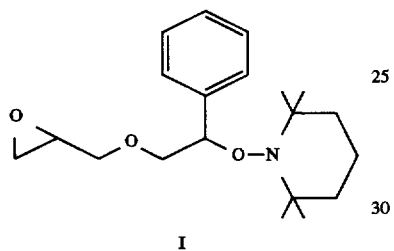

2-Phenyl-2-(2,2,6,6-tetramethylpiperidinyl-1-oxy) ethanol ($I_A$) is prepared according to the method of Hawker (C. J. Hawker and J. L. Hedrick, *Macromolecules*, 1995, 28, 2993). Epichlorohydrin (2.8 g) is added dropwise to a 100 mL round-bottomed flask containing a mixture of 50% aqueous sodium hydroxide (4.3 mL) and $Bu_4NHSO_4$ (0.085 g). The mixture is stirred vigorously at ambient temperature for 2 hours. $I_A$ (1.7 g) is added to the mixture dropwise over 1 hour with additional stirring for 16 hours. Water (30 mL) is then added and the resulting mixture is extracted with methylene chloride. Upon evaporation of the methylene chloride an oil residue remains which is crystallized from methanol to give 1.5 g of white crystal (melting point= 35°–36° C.). The product is confirmed to have the structure of compound I using NMR spectroscopy.

Step 2: Preparation of Nitroxide Terminated Polybutadiene Using Compound I

Butadiene (17.4 mmol) is added to a flask containing 10 mL cyclohexane and sec-butyllithium (0.29 mmol) and anionically polymerized while stirring under dry nitrogen for 24 hours at ambient temperature. The resulting polybutadienyl lithium is terminated by the addition of compound I (3.4 mmol) which has been dissolved in 20 mL cyclohexane. After stirring for another 24 hours at ambient temperature, methanol is added to precipitate the polybutadiene. Analysis of the polymer, using gel permeation chromatography, shows that the Mw=3930 and Mn=3840. Analysis of the polymer using $^1$H-NMR confirms that >95% of one of the polybutadiene chain-ends possess a fragment derived from compound II.

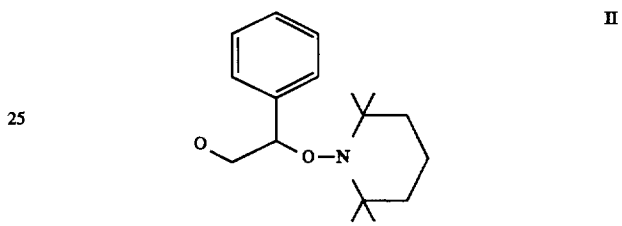

Step 3: Preparation of Transparent Impact Polystyrene

The nitroxide terminated polybutadiene rubber (1 g) prepared in Step 2 is dissolved in 20 grams of styrene. The solution (2 g) is sealed in a glass ampoule and placed in an oil bath which is heated at 140° C. for 2 hours. The ampoule is opened and the contents dissolved in 2 parts of methylene chloride. The solution is poured into a shallow pan and allowed to evaporate in a vacuum oven to give a flexible clear film. The weight of the film shows a yield of 45% transparent impact polystyrene.

EXAMPLE 2

Preparation of Transparent ABS

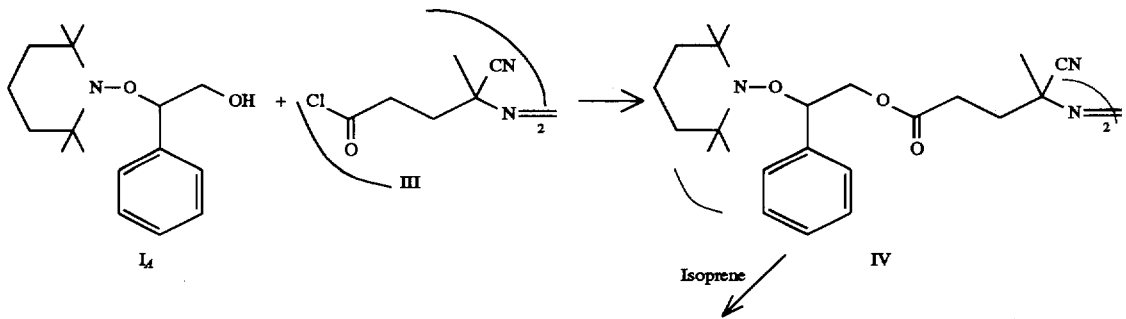

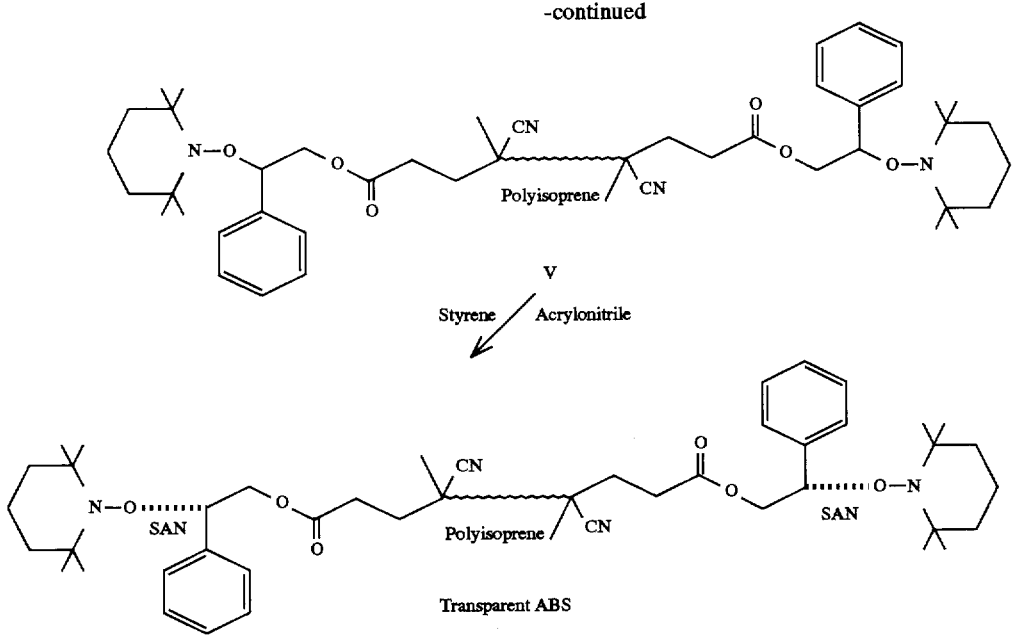

Step 1: Preparation of 4,4'-azobis[4-cyano-bis[2-phenyl-2-(2,2,6,6-tetramethyl-1-piperidinyl)oxy]ethyl] pentanoate (IV).

A 100 mL, round-bottomed flask equipped with a magnetic stirrer and nitrogen inlet is charged with 3.4 g (12 mmol) $I_A$ (prepared as in Example 1), 20 mL methylene chloride, and 0.74 g (10 mmol) pyridine. A solution of 1.58 g (5 mmol) III (prepared by the method of Onen, A.; Yagci, Y. J. Macromol. Sci., Chem. 1990, A27, 743) in 10 mL methylene chloride is added and the mixture is stirred at room temperature for approximately 30 minutes. The reaction mixture is then washed with water and dried over anhydrous sodium sulfate. The resulting solution is concentrated using rotary evaporation to yield a light yellow oil which is purified by flash chromatography on silica gel (80:20 hexane/ethyl ether followed by 60:40 hexane/ether). The product is a white crystalline solid (mp=111° C., decomposes)(yield=1.1 g, 28%). The structure of the product is confirmed as having the structure of formula IV using mass spectroscopy and NMR.

Step 2: Preparation of Nitroxide-Terminated Polyisoprene (V)

A solution (3 g) of IV (4.2 mmolar) in isoprene is sealed under vacuum in a glass ampoule. The ampoule is heated in an oil bath at 90° C. for 5 hours. The ampoule is removed and cooled to room temperature. The ampoule contents are then poured into methanol to precipitate the polymer and the polymer is dried in a vacuum oven at 50° C. for 2 hours to yield 0.18 grams of polyisoprene (V). NMR analysis confirms that the polymer contains nitroxide functionality.

Step 3: Preparation of Transparent ABS

The polyisoprene prepared in Step 2 (0.15 g) is dissolved in a mixture of styrene and acrylonitrile (75:25 w/w)(2.96 g) and the solution sealed under vacuum in a glass ampoule. The ampoule is then placed in an oil bath at 140° C. for 15 minutes. The contents of the ampoule is dissolved in 2 parts of methylene chloride. The solution is poured into a shallow pan and allowed to evaporate in a vacuum oven to give a flexible clear film. The weight of the film shows a yield of 15% transparent ABS.

What is claimed is:

1. A free radical bulk polymerization process for producing a rubber modified polymer from a vinyl aromatic monomer comprising:

contacting a conjugated diene rubber having at least one stable free radical group with a vinyl aromatic monomer, under free radical bulk polymerization conditions such that the vinyl aromatic monomer polymerizes to form a matrix phase and copolymerizes with the conjugated diene rubber such that a grafted vinyl aromatic-diene block copolymer rubber is formed in situ.

2. The process of claim 1 wherein the vinyl aromatic monomer is styrene.

3. The process of claim 2 wherein a monomer copolymerizable with the vinyl aromatic monomer is also present.

4. The process of claim 3 wherein the copolymerizable monomer is acrylonitrile.

5. The process of claim 1 wherein the stable free radical group is a nitroxy group.

6. The process of claim 1 wherein a high impact polystyrene is produced.

7. The process of claim 1 wherein an acrylonitrile-butadiene-styrene copolymer is produced.

8. The process of claim 1 wherein the diene rubber is a polybutadiene.

9. The process of claim 1 wherein the diene rubber is a polyisoprene.

10. The process of claim 1 wherein a transparent rubber modified polymer is produced.

* * * * *